(12) United States Patent
Nobis et al.

(10) Patent No.: US 7,758,593 B2
(45) Date of Patent: Jul. 20, 2010

(54) MEDICAL INSTRUMENT HANDLE AND MEDICAL INSTRUMENT HAVING SAME

(75) Inventors: Rudolph H. Nobis, Mason, OH (US); Ifung Lu, Skokie, IL (US); Omar Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 521 days.

(21) Appl. No.: 11/417,482

(22) Filed: May 4, 2006

(65) Prior Publication Data

US 2007/0260264 A1 Nov. 8, 2007

(51) Int. Cl.
*A61B 17/24* (2006.01)
*A61B 17/26* (2006.01)
(52) U.S. Cl. .............................. 606/113; 606/47
(58) Field of Classification Search ............. 606/113, 606/1, 167, 127, 139, 148, 153, 185, 205, 606/32, 41, 47, 48; 600/104, 144, 201, 562, 600/564, 565, 567
See application file for complete search history.

(56) References Cited

U.S. PATENT DOCUMENTS

| | | | |
|---|---|---|---|
| 3,470,876 A | 10/1969 | Barchilon | |
| 3,521,620 A | 7/1970 | Cook | |
| 3,791,387 A | 2/1974 | Itoh | |
| 3,799,151 A | 3/1974 | Fakaumi et al. | |
| 3,805,791 A | 4/1974 | Seuberth et al. | |
| 4,326,530 A * | 4/1982 | Fleury, Jr. ............... | 606/47 |
| 4,493,320 A | 1/1985 | Treat | |
| 4,638,802 A | 1/1987 | Okada | |
| 4,735,194 A | 4/1988 | Stiegmann | |
| 4,890,602 A | 1/1990 | Hake | |
| 4,963,147 A | 10/1990 | Agee et al. | |
| 5,002,041 A | 3/1991 | Chikama | |

(Continued)

FOREIGN PATENT DOCUMENTS

DE 19729499 1/1999

(Continued)

OTHER PUBLICATIONS

Ginsberg, G.G., "Colonoscopy with the variable stiffness colonoscope," Gastrointestinal Endoscopy, vol. 58, No. 4 (2003).

(Continued)

*Primary Examiner*—Anhtuan T Nguyen
*Assistant Examiner*—Tin Nguyen
(74) *Attorney, Agent, or Firm*—Victor C. Moreno; Gerry S. Gressel

(57) ABSTRACT

A medical instrument handle includes a medical-instrument-handle body, manually-slidable first and second slides, and medical-instrument-member first and second articulation cables. The handle body has a longitudinal axis, a proximal body portion, and a distal body portion. The first slide is slidably attached to the handle body. The first articulation cable includes a first proximal cable portion which has a first centerline and which is connected to the first slide. The second slide is slidably attached to the handle body. The second articulation cable includes a second proximal cable portion which is connected to the second slide. A medical instrument also includes a flexible shaft and a medical end effector.

19 Claims, 8 Drawing Sheets

U.S. PATENT DOCUMENTS

| | | | |
|---|---|---|---|
| 5,035,696 A | | 7/1991 | Rydell |
| 5,066,295 A | * | 11/1991 | Kozak et al. .................. 606/47 |
| 5,078,716 A | | 1/1992 | Doll |
| 5,171,314 A | | 12/1992 | Dulebohn |
| 5,201,732 A | | 4/1993 | Parins et al. |
| 5,201,741 A | | 4/1993 | Dulebohn |
| 5,250,060 A | | 10/1993 | Carbo et al. |
| 5,322,505 A | | 6/1994 | Krause et al. |
| 5,342,299 A | | 8/1994 | Snoke et al. |
| 5,346,504 A | | 9/1994 | Ortiz et al. |
| 5,353,807 A | | 10/1994 | DeMarco |
| 5,397,304 A | | 3/1995 | Truckai |
| 5,409,453 A | | 4/1995 | Lundquist et al. |
| 5,431,671 A | | 7/1995 | Nallakrishnan |
| 5,433,721 A | | 7/1995 | Hooven et al. |
| 5,441,499 A | | 8/1995 | Fritzsch |
| 5,482,029 A | | 1/1996 | Sekiguchi et al. |
| 5,522,829 A | | 6/1996 | Michalos |
| 5,531,664 A | | 7/1996 | Adachi et al. |
| 5,531,686 A | | 7/1996 | Lundquist et al. |
| 5,542,948 A | | 8/1996 | Weaver et al. |
| 5,618,294 A | | 4/1997 | Aust et al. |
| 5,706,827 A | | 1/1998 | Ehr et al. |
| 5,749,828 A | | 5/1998 | Solomon et al. |
| 5,776,080 A | | 7/1998 | Thome et al. |
| 5,792,165 A | | 8/1998 | Kileman et al. |
| 5,810,807 A | | 9/1998 | Ganz et al. |
| 5,836,947 A | | 11/1998 | Fleischman |
| 5,848,986 A | | 12/1998 | Lundquist et al. |
| 5,865,724 A | | 2/1999 | Palmer et al. |
| 5,897,554 A | | 4/1999 | Chia et al. |
| 5,972,012 A | | 10/1999 | Ream et al. |
| 6,066,102 A | | 5/2000 | Townsend et al. |
| 6,071,277 A | | 6/2000 | Farley et al. |
| 6,074,408 A | | 6/2000 | Freeman |
| 6,152,918 A | | 11/2000 | Padilla et al. |
| 6,203,494 B1 | | 3/2001 | Moriyama |
| 6,352,503 B1 | | 3/2002 | Matsui et al. |
| 6,371,907 B1 | | 4/2002 | Hasegawa et al. |
| 6,423,059 B1 | | 7/2002 | Hanson et al. |
| 6,443,943 B1 | | 9/2002 | Ouchi |
| 6,443,944 B1 | | 9/2002 | Doshi et al. |
| 6,450,948 B1 | | 9/2002 | Matsuura et al. |
| 6,451,014 B1 | | 9/2002 | Wakikaido et al. |
| 6,454,703 B1 | | 9/2002 | Ide |
| 6,454,758 B1 | | 9/2002 | Thompson |
| 6,475,222 B1 | | 11/2002 | Berg et al. |
| 6,482,149 B1 | | 11/2002 | Torii |
| 6,488,658 B1 | | 12/2002 | Long |
| 6,500,189 B1 | | 12/2002 | Lang et al. |
| 6,569,105 B1 | | 5/2003 | Kortenbach et al. |
| 6,579,300 B2 | | 6/2003 | Griego et al. |
| 6,602,267 B2 | | 8/2003 | Castaneda |
| 6,612,992 B1 | | 9/2003 | Hossack et al. |
| 6,709,388 B1 | | 3/2004 | Mosse et al. |
| 6,730,097 B2 | | 5/2004 | Dennis |
| 6,743,240 B2 | | 6/2004 | Smith et al. |
| 6,764,441 B2 | | 7/2004 | Chiel et al. |
| 6,866,626 B2 | | 3/2005 | Long et al. |
| 7,060,024 B2 | | 6/2006 | Long et al. |
| 7,060,025 B2 | | 6/2006 | Long et al. |
| 7,066,879 B2 | | 6/2006 | Fowler et al. |
| 7,093,518 B2 | | 8/2006 | Gmeilbauer |
| 7,118,587 B2 | | 10/2006 | Dycus et al. |
| 2001/0037084 A1 | | 11/2001 | Nardeo |
| 2002/0017515 A1 | | 2/2002 | Obata et al. |
| 2002/0087208 A1 | | 7/2002 | Koblish et al. |
| 2002/0095168 A1 | * | 7/2002 | Griego et al. ................ 606/167 |
| 2002/0147445 A1 | | 10/2002 | Farley et al. |
| 2002/0177802 A1 | | 11/2002 | Moutafis et al. |
| 2003/0045778 A1 | | 3/2003 | Ohline et al. |
| 2003/0074014 A1 | | 4/2003 | Castaneda |
| 2003/0109898 A1 | | 6/2003 | Schwarz et al. |
| 2003/0125788 A1 | | 7/2003 | Long |
| 2003/0153866 A1 | | 8/2003 | Long et al. |
| 2003/0181785 A1 | | 9/2003 | Viebach et al. |
| 2003/0195492 A1 | * | 10/2003 | Gobron et al. ................. 606/1 |
| 2003/0208219 A1 | | 11/2003 | Aznoian et al. |
| 2004/0034343 A1 | | 2/2004 | Gillespie et al. |
| 2004/0044350 A1 | | 3/2004 | Martin et al. |
| 2004/0068291 A1 | | 4/2004 | Suzuki |
| 2004/0092953 A1 | | 5/2004 | Salameh et al. |
| 2004/0097919 A1 | | 5/2004 | Wellman et al. |
| 2004/0143159 A1 | | 7/2004 | Wendlandt |
| 2004/0193016 A1 | | 9/2004 | Root et al. |
| 2004/0230096 A1 | | 11/2004 | Stefanchik et al. |
| 2005/0043743 A1 | | 2/2005 | Dennis |
| 2005/0183733 A1 | | 8/2005 | Kawano et al. |
| 2005/0222587 A1 | | 10/2005 | Jinno et al. |
| 2005/0234296 A1 | | 10/2005 | Saadat et al. |
| 2005/0272975 A1 | | 12/2005 | McWeeney et al. |
| 2005/0273084 A1 | | 12/2005 | Hinmen et al. |
| 2005/0273085 A1 | | 12/2005 | Hinman et al. |
| 2006/0009711 A1 | | 1/2006 | Gingrich et al. |
| 2006/0089627 A1 | | 4/2006 | Burnett et al. |

FOREIGN PATENT DOCUMENTS

| | | |
|---|---|---|
| EP | 0027704 | 4/1981 |
| EP | 0397489 | 11/1990 |
| EP | 1310206 | 5/2003 |
| EP | 1849421 | 10/2007 |
| JP | 59-181124 | 10/1984 |
| JP | 2004-154164 | 6/2004 |
| WO | WO 96/00030 | 1/1996 |
| WO | WO 97/12557 | 4/1997 |
| WO | 97/35135 | 9/1997 |
| WO | 99/12489 | 3/1999 |
| WO | 01/08737 | 2/2001 |
| WO | 01/82814 | 11/2001 |
| WO | 01/93938 | 12/2001 |
| WO | 02/43797 | 6/2002 |
| WO | 03/053225 | 7/2003 |
| WO | 2005/113051 | 12/2005 |
| WO | 2006/019291 | 2/2006 |
| WO | 2006/122279 | 11/2006 |

OTHER PUBLICATIONS

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," Endoscopy; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

Examination Report, European Application No. 07251728.7 (Dec. 17, 2008).

European Search Report, European Application No. 07251934 (2 pages) (dated Aug. 30, 2007).

* cited by examiner

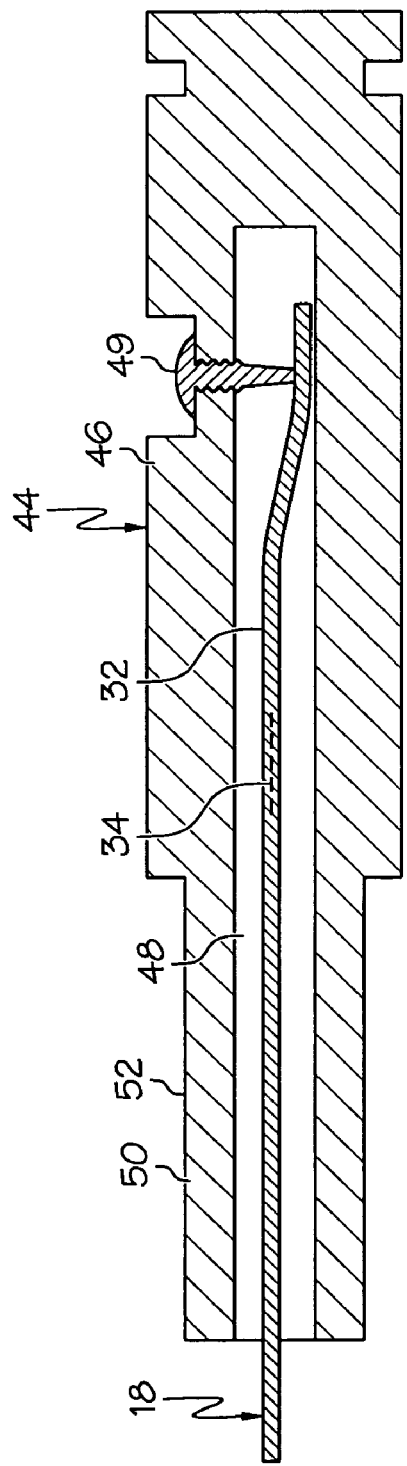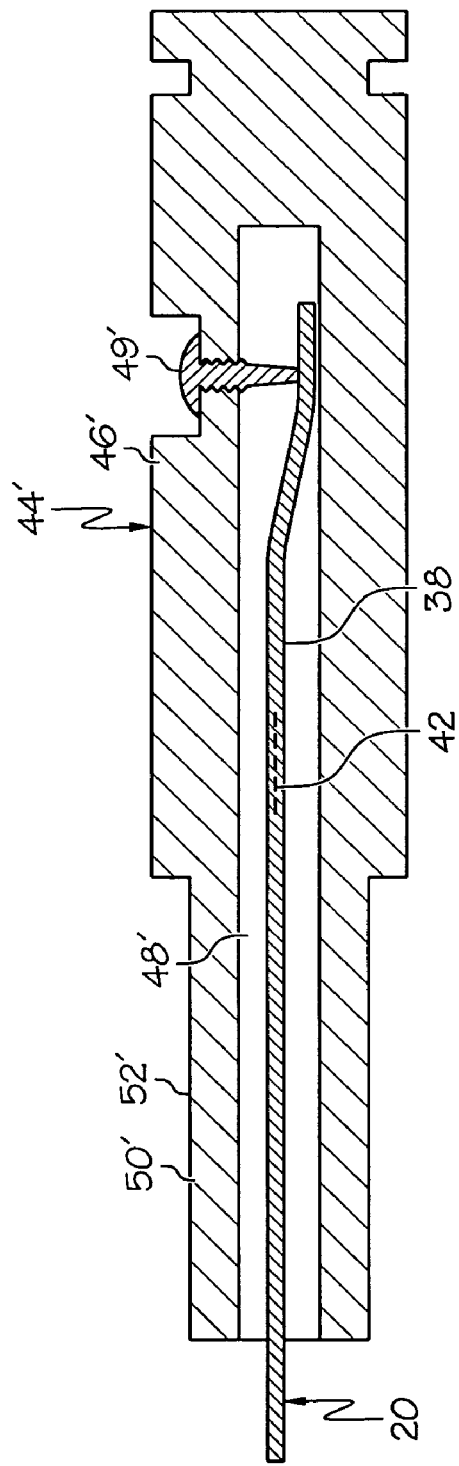

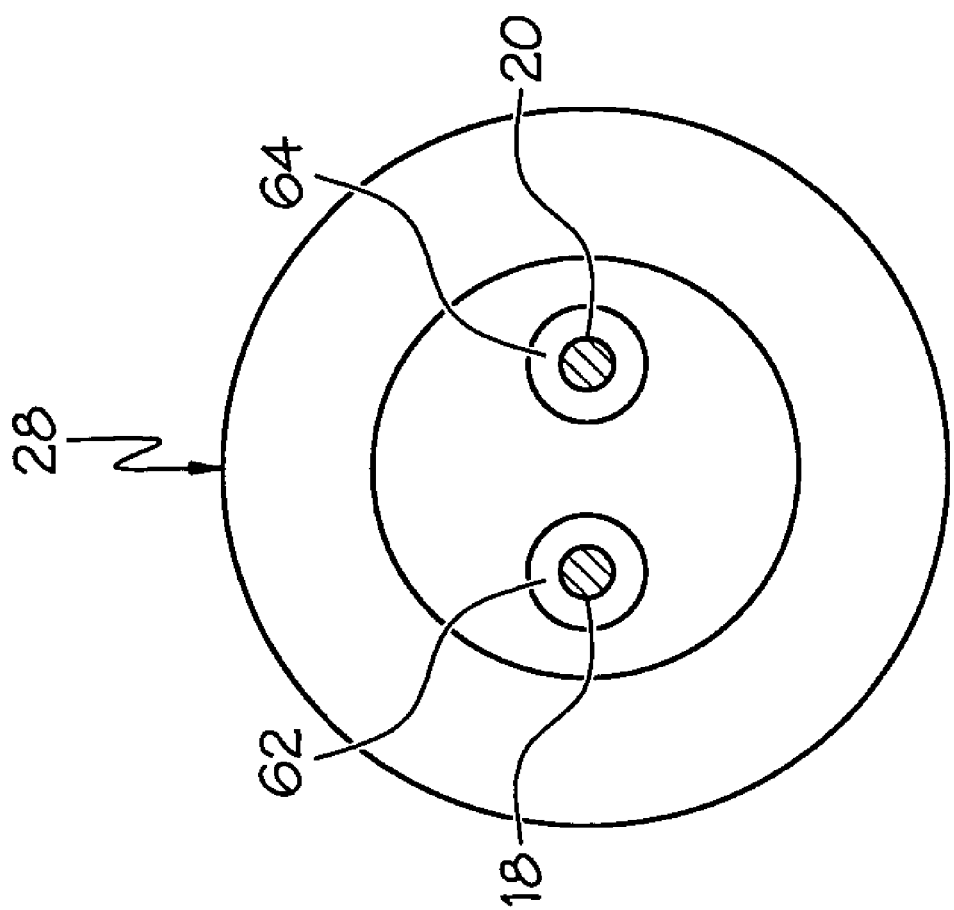

MEDICAL INSTRUMENT HANDLE AND MEDICAL INSTRUMENT HAVING SAME

FIELD OF THE INVENTION

The present invention is related generally to medical equipment, and more particularly to a medical instrument handle and to a medical instrument having a handle.

BACKGROUND OF THE INVENTION

Endoscopes (including colonoscopes) are known which have an insertion tube which is insertable within a patient. The insertion tube has an articulatable distal end portion controlled by wires running from the distal end portion to control knobs on the handle of the endoscope. A wide angle video camera in the distal end of the insertion tube permits medical observation. Medical devices, such as a medical needle-knife or a medical snare, are part of an endoscopic system and are insertable into the working channel(s) of the insertion tube of the endoscope and are translatable to extend from the distal end portion for medical treatment. Other medical devices are known which use a manually-pulled pull wire, surrounded by a flexible sheath connected to a handle, to articulate an end effector about a pivot pin.

A medical needle-knife assembly is known which includes a medical needle-knife attached to a wire with both needle-knife and wire surrounded by a shaft. The shaft is insertable into a working channel of the insertion tube of the endoscope and is translatable to the distal end portion of the endoscope insertion tube. Then, the wire is lengthwise translated to extend the medical needle-knife from the shaft and from the distal end portion of the endoscope insertion tube. Then, in one example, the medical needle-knife is used to provide medical treatment by energizing the wire with energy from a radio-frequency generator.

A medical snare assembly is known which includes a stainless-steel wire having a lengthwise translatable first end and having a second end which is fixedly attached to the wire after forming a distal-loop medical snare. Another medical snare assembly is known which includes a stainless-steel wire having a lengthwise translatable first end and having a second end which is fixedly attached to a handpiece after forming a distal-loop medical snare. The wire including the distal-loop medical snare is insertable into a working channel of the insertion tube of the endoscope, and the first end is lengthwise translated to extend the medical snare from the distal end portion of the endoscope insertion tube. Then, in one example, the medical snare is used to provide medical treatment by energizing the wire with energy from a radio-frequency generator. Known distal-loop medical snares come in a variety of fixed treatment shapes with a particular treatment shape chosen for a particular application.

Still, scientists and engineers continue to seek improved medical instrument handles and medical instruments having a handle.

SUMMARY OF THE INVENTION

A first expression of an embodiment of the invention is for a medical instrument handle including a medical-instrument-handle body, manually-slidable first and second slides, and medical-instrument-member first and second articulation cables. The handle body has a longitudinal axis, a proximal body portion, and a distal body portion. The first slide is slidably attached to the handle body. The first articulation cable includes a first proximal cable portion which has a first centerline and which is connected to the first slide. The second slide is slidably attached to the handle body. The second articulation cable includes a second proximal cable portion which is connected to the second slide.

A second expression of an embodiment of the invention is for a medical instrument including a medical instrument handle as described in the previous paragraph, a flexible shaft, and a medical end effector. The shaft has a shaft length, a proximal shaft end attached to the distal body portion, a distal shaft end insertable within a patient, and first and second shaft lumens extending from the proximal shaft end at least a majority of the shaft length toward the distal shaft end. The first articulation cable is disposed in the first shaft lumen, and the second articulation cable is disposed in the second shaft lumen. The first articulation cable includes a first distal cable portion operatively connected to the medical end effector to articulate the medical end effector, and the second articulation cable includes a second distal cable portion operatively connected to the medical end effector to articulate the medical end effector.

Several benefits and advantages are obtained from one or more of the expressions of an embodiment of the invention. In one example, wherein the medical end effector includes a medical needle-knife or a medical snare, distally moving the first and second slides together extends the medical end effector from the shaft, proximally moving the first and second slides together retracts the medical end effector into the shaft, distally moving only the first slide articulates the medical end effector to a first side, and distally moving only the second slide articulates the medical end effector to a second side which is opposite to the first side. In the same or a different example, wherein the medical end effector includes a medical needle-knife or a medical snare which lies substantially in a plane when in a relaxed state, the medical instrument handle also includes a ring substantially coaxially aligned with the longitudinal axis, rotatably attached to the handle body, and adapted to rotate the first proximal cable portion about the first centerline wherein rotation of the ring articulates the extended medical needle-knife and extended medical snare out of the plane and changes the shape of the extended medical snare. In one procedure involving a medical snare, a user articulates the medical snare to assume different treatment shapes without having to use two different conventional medical snares having two different fixed treatment shapes. In a first application, the distal shaft portion is inserted into a working channel of a flexible insertion tube of an endoscope, wherein the medical end effector can be articulated with respect to the insertion tube of the endoscope allowing independent alignment of the wide angle video camera of the endoscope and the medical end effector. In a second application, the distal shaft portion is adapted to be coupled to, and slid along, an exterior rail of a flexible insertion tube of an endoscope allowing independent alignment of the wide angle video camera of the endoscope and the medical end effector.

BRIEF DESCRIPTION OF THE FIGURES

FIGS. 4A and 4B are enlarged cross-sectional views of the first and second proximal rod portions showing the first and second articulation cables attached respectively to the first and second proximal rod portions;

FIG. 5 is a front elevational view of the distal body portion with the shaft removed and with the distal cable portions shown in cross section;

DETAILED DESCRIPTION OF THE INVENTION

Figure 1:
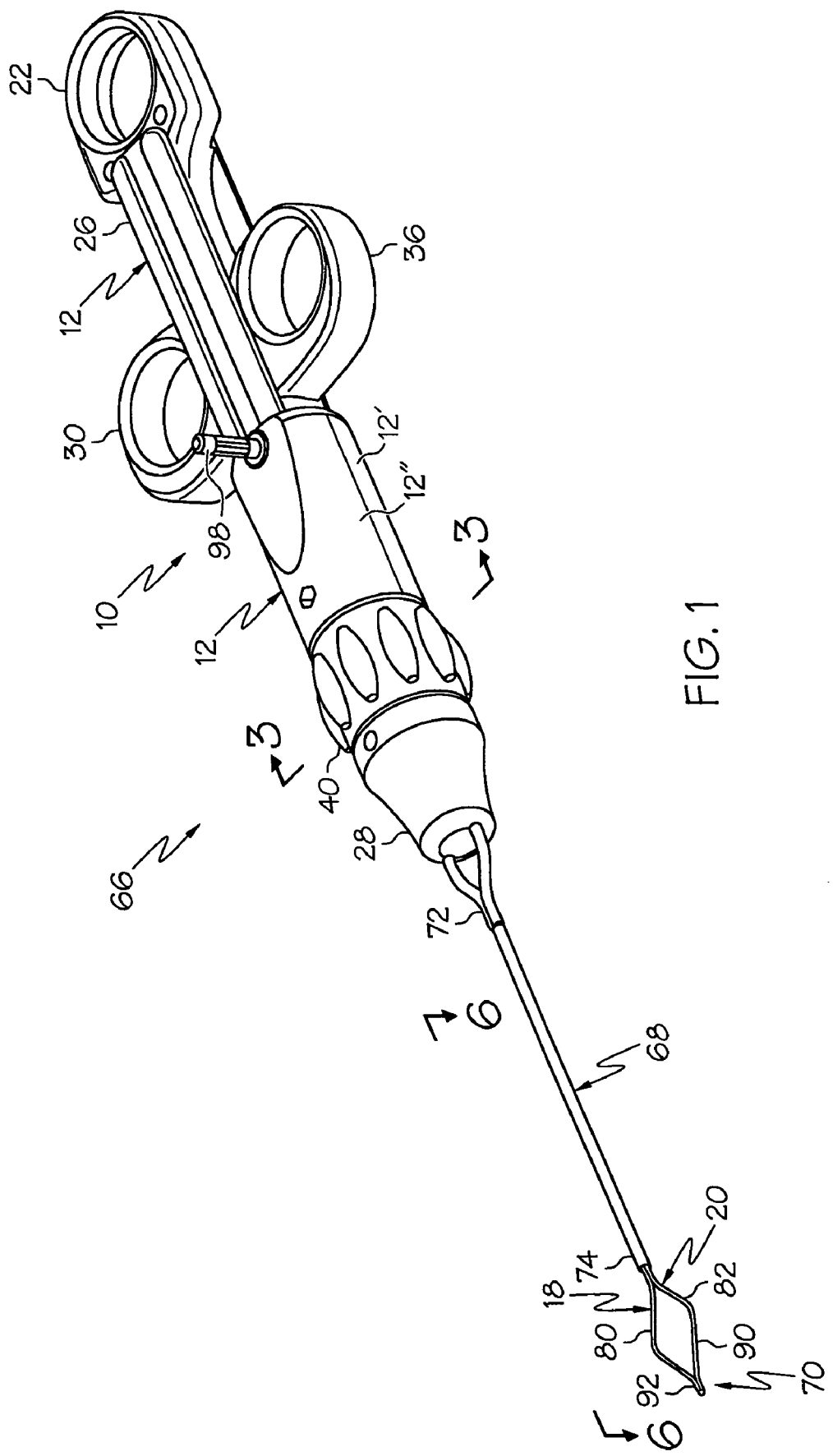
FIG. 1 is a perspective view of an embodiment of a medical instrument including a medical instrument handle, a flexible shaft, and a medical end effector which includes a medical needle-knife.
Figure 2:
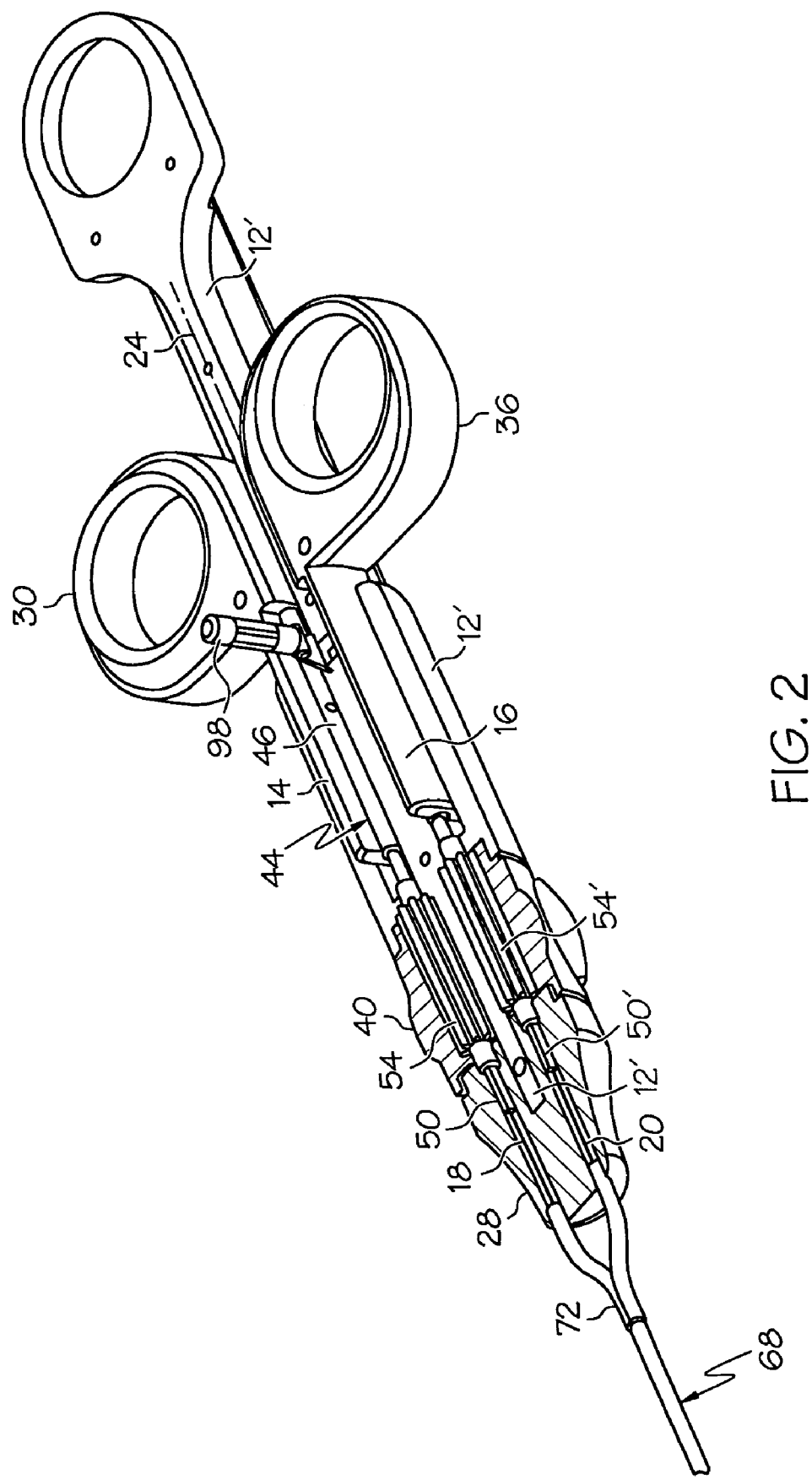
FIG. 2 is partial-assembly perspective view of the medical instrument handle of FIG. 1, wherein the handle body, except for the distal body portion, is constructed of two longitudinally-split halves, wherein the top half has been removed, and wherein the distal body portion and the ring have been cut and shown in cross section.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is understood that any one or more of the following-described expressions of embodiments, examples, etc. can be combined with any one or more of the other following-described expressions of embodiments, examples, etc.

Referring now to the figures, wherein like numerals represent like elements throughout, FIGS. 1-6 illustrate an embodiment of the invention. A first expression of the embodiment of FIGS. 1-6 is for a medical instrument handle 10 including a medical-instrument-handle body 12, manually-slidable first and second slides 14 and 16, and medical-instrument-member first and second articulation cables 18 and 20. The handle body 12 has a longitudinal axis 24, a proximal body portion 26, and a distal body portion 28. The first slide 14 is slidably attached to the handle body 12. The first articulation cable 18 includes a first proximal cable portion 32 which has a first centerline 34 and which is connected to the first slide 14. The second slide 16 is slidably attached to the handle body 12. The second articulation cable 20 includes a second proximal cable portion 38 which is connected to the second slide 16. It is noted that a "medical-instrument-member" includes, but is not limited to a medical end effector.

In one extension of the first expression of the embodiment of FIGS. 1-6, the medical instrument handle 10 also includes a ring 40 substantially coaxially aligned with the longitudinal axis 24, rotatably attached to the handle body 12 and operatively connected to the first proximal cable portion 32 to rotate the first proximal cable portion 32 substantially about the first centerline 34. In a first variation, the second proximal cable portion 38 has a second centerline 42, wherein the ring 40 is operatively connected to the second proximal cable portion 38 to rotate the second proximal cable portion 38 substantially about the second centerline 42. In one modification, the ring 40 is operatively connected to the first and second proximal cable portions 32 and 38 to rotate the first and second proximal cable portions 32 and 38 in a same rotational direction. For example, in FIG. 3, clockwise rotation of the ring 40 rotates both the first and second proximal cable portions 32 and 38 in the clockwise direction. In a second variation, not shown, the ring is not operatively connected to the second proximal cable portion so the ring cannot rotate the second proximal cable portion substantially about its centerline.

In one construction of the first expression of the embodiment of FIGS. 1-6, the first and second slides 14 and 16 are substantially diametrically opposed about the longitudinal axis 24. In the same or a different construction, not shown, the medical instrument handle includes at least one additional slide and medical-instrument-member articulation cable and/or medical end effector activation cable connected thereto. Examples of cables include, without limitation, a wire. Types of wire include, without limitation, braided wire, monolithic wire, and wire segments lengthwise attached end to end. It is noted that a monolithic wire is one continuous piece. Other examples of cables and types of wire are left to those skilled in the art. In one choice of materials, the first and second articulation cables 18 and 20 consist essentially of nitinol wire. It is noted that nitinol wire is a superelastic wire.

Figure 3:
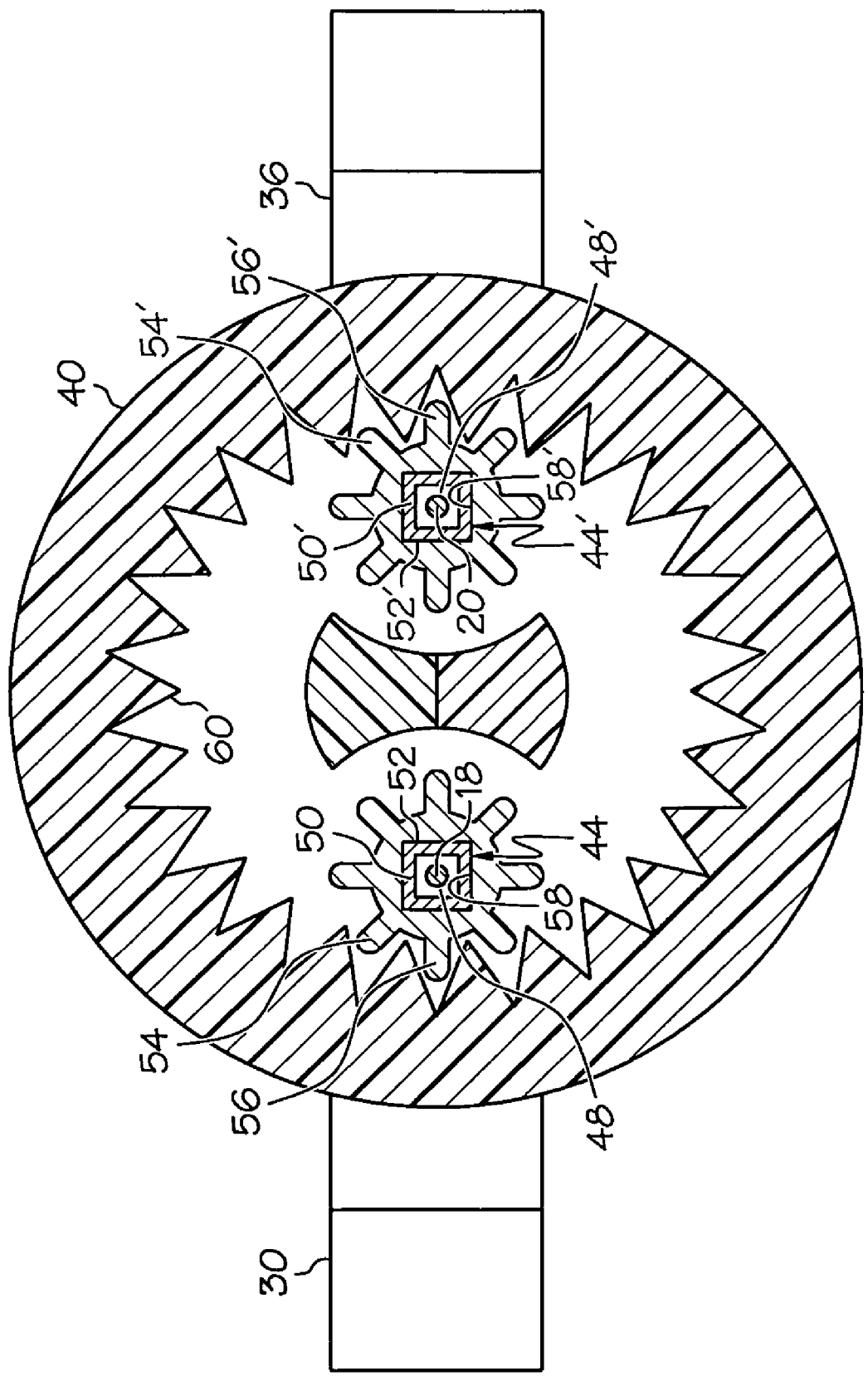
FIG. 3 is a cross-sectional view of the embodiment of FIG. 1 taken along lines 3-3 of FIG. 1, with the banana plug removed for clarity.
Figure 6:
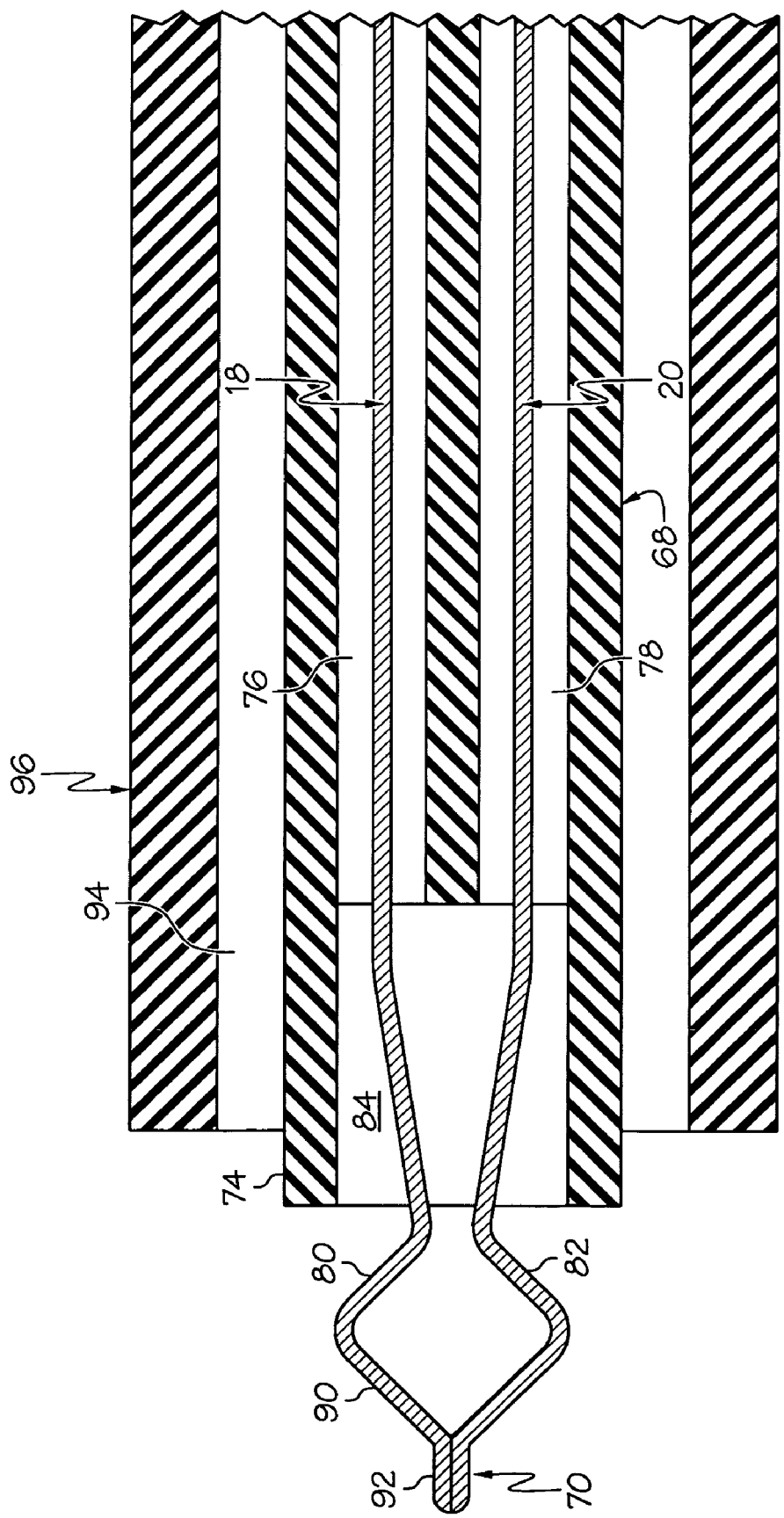
FIG. 6 is an enlarged cross-sectional view of the shaft of the embodiment of FIG. 1 taken along lines 6-6 of FIG. 1 also showing the distal shaft portion inserted within a working channel of an endoscope insertion tube, wherein the endoscope handle and operational features (such as insertion tube articulation features and a wide angle video camera) of the endoscope insertion tube have been omitted for clarity.

In one enablement of the first expression of the embodiment of FIGS. 1-6, the medical instrument handle 10 also includes a first rod 44 having a first proximal rod portion 46 rotatably attached to the first slide 14 and having a first rod lumen 48, wherein the first proximal cable portion 32 is disposed within the first rod lumen 48 and is non-rotatably attached to the first rod 44 such as, without limitation, by a first set screw 49. In one variation, the first rod 44 has a first distal rod portion 50 having a longitudinally-elongated first keyed outer surface 52 (such as, but not limited, to a square outer surface as shown in FIG. 3). In one modification, the medical instrument handle 10 also includes a first pinion gear 54 having longitudinally-elongated first teeth 56 and having a first keyhole lumen 58 engaging the first keyed outer surface 52 of the first distal rod portion 50, wherein the ring 40 has an inner circumferential array of longitudinally-elongated ring teeth 60 engaging the first teeth 56. In one illustration, the ring 40 is disposed between the first finger ring 30 and the distal body portion 28.

In the same or a different enablement, the medical instrument handle 10 includes a second rod 44' having a second proximal rod portion 46', a second rod lumen 48', a second set screw 49', and a second distal rod portion 50' with a second keyed outer surface 52' and includes a second pinion gear 54' having second teeth 56' and a second keyhole lumen 58' similar to the first rod 44 and the first pinion gear 54.

In one employment of the first expression of the embodiment of FIGS. 1-6, the medical instrument 10 also includes an electrical connector 98, wherein the first proximal cable portion 32 is in electrical contact with the electrical connector 98. In the same or a different employment, the distal body portion 28 has first and second passageways 62 and 64, wherein the first articulation cable 18 extends from the first passageway 62 and the second articulation cable 20 extends from the second passageway 64.

In a first arrangement of the first expression of the embodiment of FIGS. 1-6, a proximal finger ring 30 is monolithically attached to the proximal body portion 26. Thus, in this arrangement, the proximal finger ring 30 and the proximal body portion 26 are two portions of one continuous piece. In a second arrangement, the handle body 12, except for the distal body portion 28, is constructed of two longitudinally-split halves 12' and 12" for ease of assembly. In a third arrangement, not shown, the proximal finger ring is rotatably attached to the proximal body portion allowing for ergonomic positioning of the hand of a user while using the first and second finger rings. In one variation of any arrangement, the first slide 14 has a first finger ring 30, and the second slide 16 has a second finger ring 36.

A second expression of the embodiment of FIGS. 1-6 is for a medical instrument 66 including a medical instrument handle 10 as described in paragraph [0024], a flexible shaft 68, and a medical end effector 70. The shaft 68 has a shaft length, a proximal shaft end 72 attached to the distal body portion 28, a distal shaft end 74 insertable within a patient, and first and second shaft lumens 76 and 78 extending from the proximal shaft end 72 at least a majority of the shaft length toward the distal shaft end 74. The first articulation cable 18 is disposed in the first shaft lumen 76, and the second articulation cable 20 is disposed in the second shaft lumen 78. The first articulation cable 18 includes a first distal cable portion 80 operatively connected to the medical end effector 70 to articulate the medical end effector 70. The second articulation cable 20 includes a second distal cable portion 82 operatively connected to the medical end effector 70 to articulate the medical end effector 70.

In one example, having the first and second shaft lumens 76 and 78 eliminates twisting of the first and second articulation cables 18 and 20 around each other, reduces friction between each articulation cable, and allows rotation of individual articulation cables while giving the user the ability, by rotating the handle body 12 about the longitudinal axis 24, to orient the medical end effector 70 to an optimal position.

It is noted that the extensions, constructions, enablements, etc. of the first expression of the embodiment of FIGS. 1-6 are equally applicable to the second expression of the embodiment of FIGS. 1-6. In one configuration of the second expression of the embodiment of FIGS. 1-6, the shaft 68 has a distal shaft lumen 84 extending from the distal shaft end 74 toward the proximal shaft end 72 and in communication with each of the first and second shaft lumens 76 and 78, wherein the medical end effector 70 is retractable into the distal shaft lumen 84 and is extendable from the distal shaft lumen 84.

In a first application of the second expression of the embodiment of FIGS. 1-6, the second distal cable portion 82 is attached (monolithically or otherwise) to the first distal cable portion 80, wherein the attached first and second distal cable portions 80 and 82 define a distal loop 90. The medical instrument 66 also includes a medical needle-knife 92 attached (monolithically otherwise) to the distal loop 90, wherein the medical end effector 70 includes the medical needle-knife 92, and wherein the distal shaft end 74 is insertable within a working channel 94 of an endoscope insertion tube 96.

In one employment of the medical needle-knife 92, the second distal cable portion 82 is monolithically attached to the first distal cable portion 80 meaning that the first and second distal cable portions 80 and 82 are monolithic portions of, for example, a nitinol wire. It is noted that nitinol wire is a superelastic wire having shape memory properties wherein the nitinol wire can have a desired shape set into the wire and wherein after flexing the wire, the wire will resiliently return to its set shape, as is known to those skilled in the art. It is noted that the distal loop 90 has a relaxed state (i.e., a state wherein the distal loop 90 it is not subject to a force and wherein the distal loop 90 is not subject to a torque). In a first example, the distal loop 90 has a substantially kite shape in the relaxed state. Applicants have found that a kite shape of the distal loop 90 improves the articulation of the medical needle-knife 92. It is noted that a kite shape is a diamond shape having two shorter sides extending from the top (distal) vertex of the diamond shape and having two longer sides extending from the bottom (proximal) vertex of the diamond shape. In one employment, the medical needle-knife 92 is a radio-frequency-energized medical needle-knife (with other portions of, for example, the nitinol wire capable of contact with the patient being electrically isolated from the patient). In one deployment, an electrical connector 98 (such as, without limitation, a banana plug) is attached to the handle body 18, wherein translating the first slide 14 causes the first rod 44 to make sliding electrical contact with the electrical connector 98, and wherein, although not shown in the figures, a wire from a radio-frequency (RF) generator is electrically attachable to the banana plug. Examples of other-energized and non-energized medical needle-knives are left to the artisan.

In one procedure, both the first and second slides 14 and 16 are lengthwise translated to retract the medical needle-knife 92 within the distal shaft lumen 84 before the shaft 68 is inserted within a patient (such as before the shaft 68 is inserted within a working channel 94 of an endoscope insertion tube 96 which has been inserted within a patient). When the distal shaft end 74 has been positioned proximate the target tissue requiring medical treatment, both the first and second slides 14 and 16 are lengthwise translated to extend the medical needle-knife 92 from the distal shaft lumen 84 (and from the endoscope insertion tube 96, if present). Thereafter, the medical needle-knife 92 is articulated to a desired orientation and/or shape for medical treatment.

Figure 7:
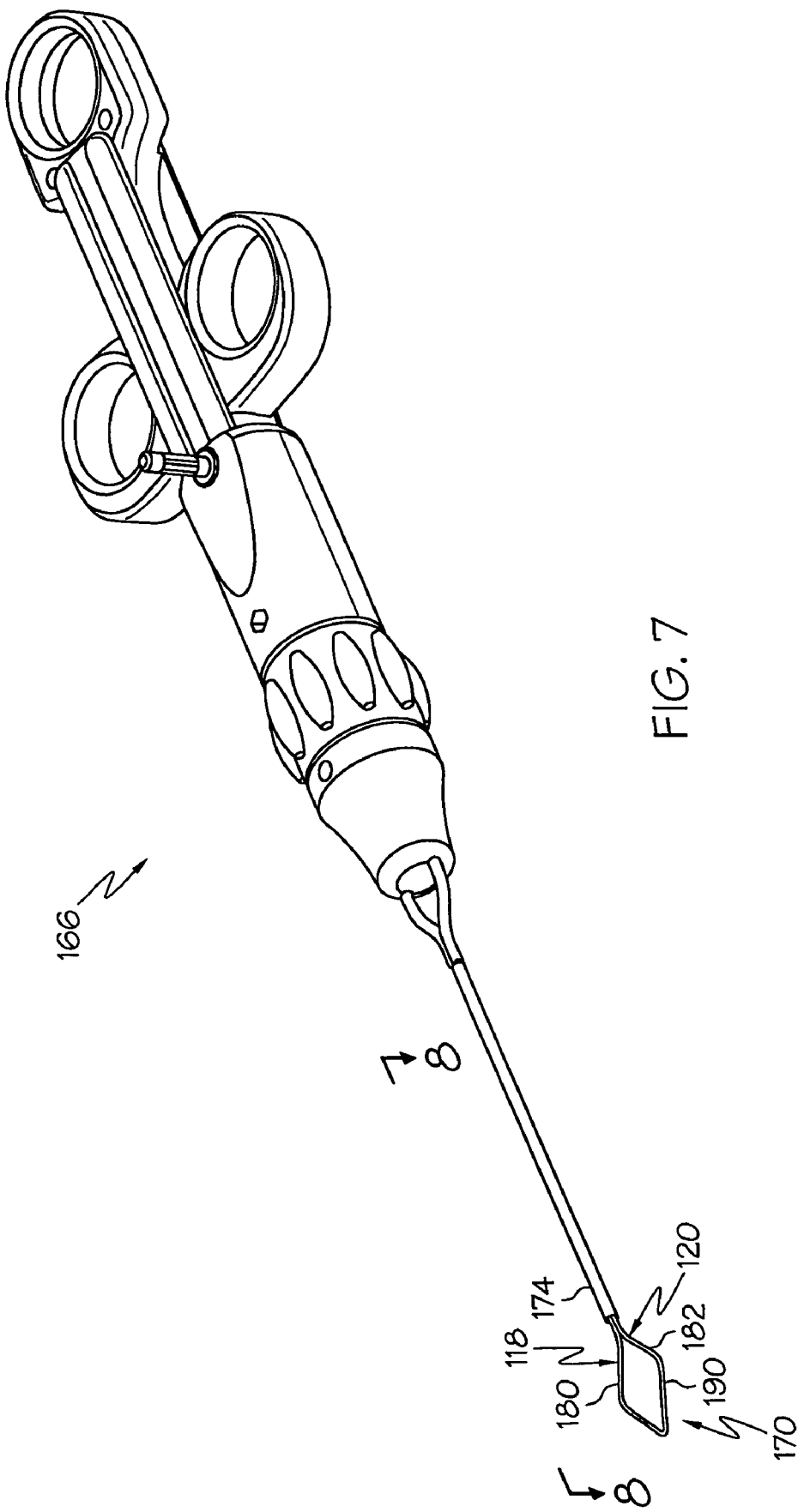
FIG. 7 is a view, as in FIG. 1, but of an alternate embodiment of the medical instrument of FIG. 1 showing an alternate medical end effector which includes a medical snare.
Figure 8:
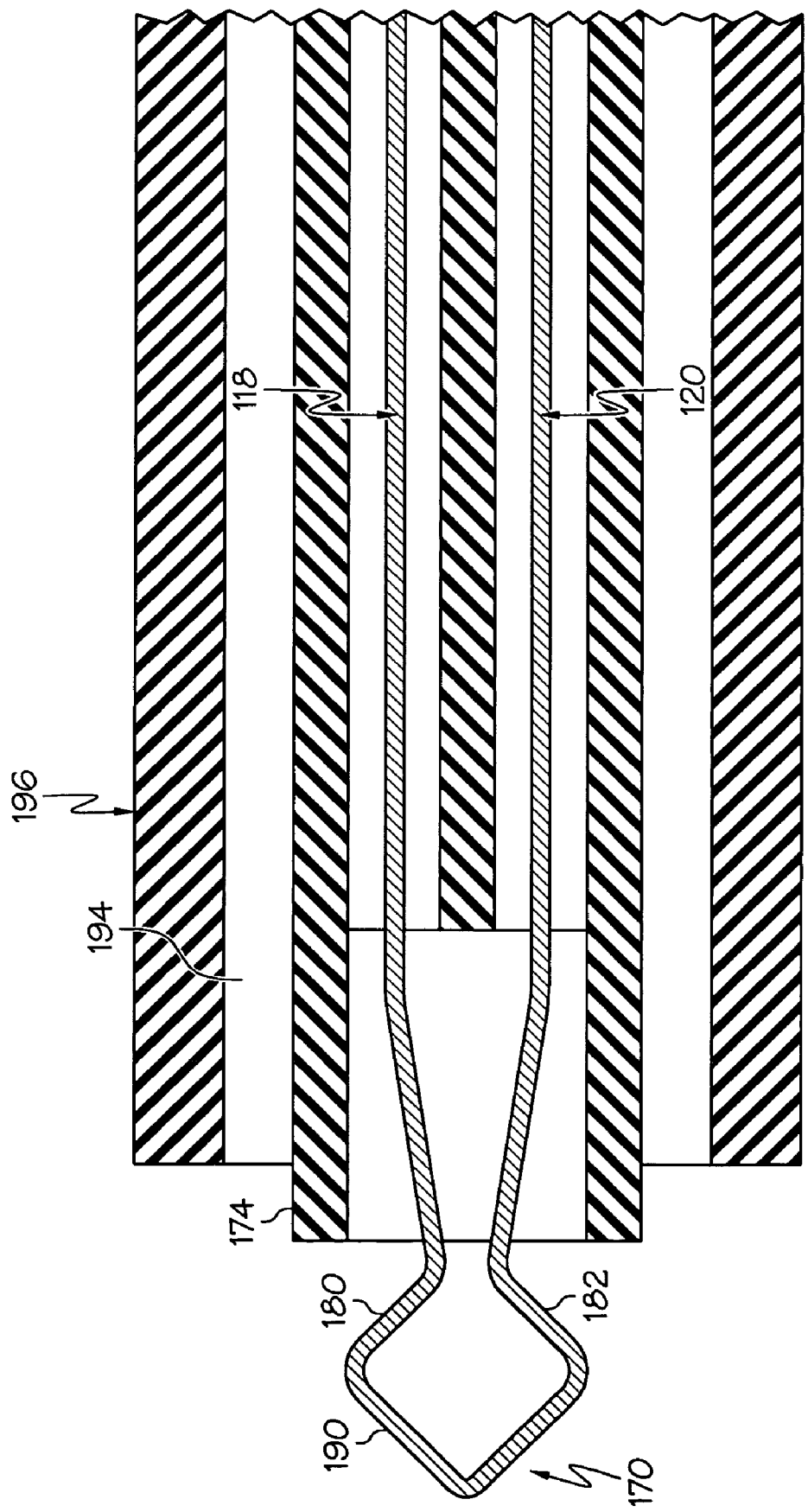
FIG. 8 is an enlarged cross-sectional view of the alternate embodiment of FIG. 7 taken along lines 8-8 of FIG. 7.

In a first alternate application, as shown in the alternate embodiment of the medical instrument 166 of FIGS. 7-8, the second distal cable portion 182 is attached to the first distal cable portion 180, wherein the attached first and second distal cable portions 180 and 182 define a distal-loop medical snare 190, wherein the medical end effector 170 includes the medical snare 190, and wherein the distal shaft end 174 is insertable within a working channel 194 of an endoscope insertion tube 196. In one example, the medical snare 190 has a substantially kite shape in a relaxed state. In the same or a different example, the medical snare 190 is a radio-frequency-energized medical snare.

In a second alternate application, not shown, the medical end effector includes a medical grasper, wherein the distal shaft end is attached to the medical grasper and wherein an additional slide is attached to an activation cable which is used to open and close the medical grasper. Other types of medical end effectors and examples of medical instrument members (other than medical end effectors) articulated by the articulation cables are left to those skilled in the art.

Several benefits and advantages are obtained from one or more of the expressions of an embodiment of the invention. In one example, wherein the medical end effector includes a medical needle-knife or a medical snare, distally moving the first and second slides together extends the medical end effector from the shaft, proximally moving the first and second slides together retracts the medical end effector into the shaft, distally moving only the first slide articulates the medical end effector to a first side, and distally moving only the second slide articulates the medical end effector to a second side which is opposite to the first side. In the same or a different example, wherein the medical end effector includes a medical needle-knife or a medical snare which lies substantially in a plane when in a relaxed state, the medical instrument handle also includes a ring substantially coaxially aligned with the longitudinal axis, rotatably attached to the handle body, and adapted to rotate the first proximal cable portion about the first centerline wherein rotation of the ring articulates the extended medical needle-knife and extended medical snare out of the plane and changes the shape of the extended medical snare. In one procedure involving a medical snare, a user articulates the medical snare to assume different treatment shapes without having to use two different conventional medical snares having two different fixed treatment shapes. In a first application, the distal shaft portion is inserted into a working channel of a flexible insertion tube of an endoscope, wherein the medical end effector can be articulated with respect to the insertion tube of the endoscope allowing independent alignment of the wide angle video camera of the endoscope and the medical end effector. In a second application, the distal shaft portion is adapted to be coupled to, and slid along, an exterior rail of a flexible insertion tube of an endoscope allowing independent alignment of the wide angle video camera of the endoscope and the medical end effector.

While the present invention has been illustrated by a description of several expressions of embodiments, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended claims.

What is claimed is:

1. A medical instrument handle comprising:
    a medical-instrument-handle body having a longitudinal axis, a proximal body portion, and a distal body portion;
    a medical-instrument-member comprising a first articulation cable and a second articulation cable;
    a manually-slidable first slide slidably attached to the handle body;
    the first articulation cable of the medical-instrument-member including a first proximal cable portion which has a first centerline and which is connected to the first slide;
    a manually-slidable second slide slidably attached to the handle body;
    the second articulation cable of the medical-instrument-member including a second proximal cable portion which is connected to the second slide;
    a ring forming a portion of the medical-instrument-handle body and housing at least a portion of the first proximal cable portion of the first articulation cable;
    a first rod having a first proximal rod portion rotatably attached to the first slide and having a first rod lumen and having a first distal rod portion having a longitudinally-elongated first keyed outer surface, wherein the first proximal cable portion is disposed within the first rod lumen and is non-rotatably attached to the first rod; and
    a first pinion gear having longitudinally-elongated first teeth and having a first keyhole lumen engaging the first keyed outer surface of the first distal rod portion;
    wherein the ring has an inner circumferential array of longitudinally-elongated ring teeth engaging the first teeth;
    wherein the ring is operatively connected to the first proximal cable portion to rotate the first proximal cable portion substantially about its centerline relative to the medical-instrument-handle body as the ring is rotated about the longitudinal axis of the medical-instrument-handle body relative to any other portion of the medical-instrument-handle body.

2. The medical instrument handle of claim 1, wherein the ring is substantially coaxially aligned with the longitudinal axis of the medical-instrument-handle body.

3. The medical instrument handle of claim 2, wherein the first and second slides are substantially diametrically opposed about the longitudinal axis.

4. The medical instrument handle of claim 2, wherein the second proximal cable portion has a second centerline, and wherein the ring is operatively connected to the second proximal cable portion to rotate the second proximal cable portion substantially about its centerline as the ring is rotated about the longitudinal axis of the medical-instrument-handle body relative to any other portion of the medical-instrument-handle body.

5. The medical instrument handle of claim 4, wherein the ring is adapted to rotate the first and second proximal cable portions in a same rotational direction.

6. The medical instrument handle of claim 1, also including an electrical connector, wherein the first proximal cable portion is in electrical contact with the electrical connector.

7. The medical instrument handle of claim 1, wherein the distal body portion has first and second passageways, wherein the first articulation cable extends from the first passageway and the second articulation cable extends from the second passageway.

8. The medical instrument handle of claim 1, wherein the first slide and the second slide are movable together to extend and retract the medical-instrument member, and the first slide and the second slide are movable relative to one another where distally moving only the first slide or only the second slide distally moves only the first articulation cable or only the second articulation cable respectively and proximally moving only the first slide or only the second slide proximally moves only the first articulation cable or only the second articulation cable respectively.

9. A medical instrument comprising:
    a) medical instrument handle including:
        a medical-instrument-handle body having a longitudinal axis, a proximal body portion, and a distal body portion;
        a medical-instrument-member comprising a first articulation cable and a second articulation cable;
        a manually-slidable first slide slidably attached to the handle body;
        the first articulation cable of the medical-instrument-member including a first proximal cable portion which has a first centerline and which is connected to the first slide;
        a manually-slidable second slide slidably attached to the handle body;
        the second articulation cable of the medical-instrument-member including a second proximal cable portion which is connected to the second slide; and
        a ring forming a portion of the medical-instrument-handle body and housing at least a portion of the first proximal cable portion of the first articulation cable;
        a first rod having a first proximal rod portion rotatably attached to the first slide and having a first rod lumen and having a first distal rod portion having a longitudinally-elongated first keyed outer surface, wherein the first proximal cable portion is disposed within the first rod lumen and is non-rotatably attached to the first rod; and
        a first pinion gear having longitudinally-elongated first teeth and having a first keyhole lumen engaging the first keyed outer surface of the first distal rod portion;

wherein the ring has an inner circumferential array of longitudinally-elongated ring teeth engaging the first teeth;

wherein the ring is operatively connected to the first proximal cable portion to rotate the first proximal cable portion substantially about its centerline relative to the medical-instrument-handle body as the ring is rotated about the longitudinal axis of the medical-instrument-handle body relative to any other portion of the medical-instrument-handle body;

b) a flexible shaft having a shaft length, a proximal shaft end attached to the distal body portion, a distal shaft end insertable within a patient, and first and second shaft lumens extending from the proximal shaft end at least a majority of the shaft length toward the distal shaft end, wherein the first articulation cable is disposed in the first shaft lumen, and wherein the second articulation cable is disposed in the second shaft lumen; and c) a medical end effector, wherein the first articulation cable includes a first distal cable portion operatively connected to the medical end effector to articulate the medical end effector, and wherein the second articulation cable includes a second distal cable portion operatively connected to the medical end effector to articulate the medical end effector.

10. The medical instrument of claim 9, wherein the ring is substantially coaxially aligned with the longitudinal axis of the medical-instrument-handle body.

11. The medical instrument of claim 9, wherein the shaft has a distal shaft lumen extending from the distal shaft end toward the proximal shaft end and in communication with each of the first and second shaft lumens, wherein the medical end effector is retractable into the distal shaft lumen and is extendable from the distal shaft lumen.

12. The medical instrument of claim 11, wherein the ring is substantially coaxially aligned with the longitudinal axis of the medical-instrument-handle body.

13. The medical instrument of claim 12, wherein the second distal cable portion is attached to the first distal cable portion, wherein the attached first and second distal cable portions define a distal loop, and also including a medical needle-knife attached to the distal loop, wherein the medical end effector includes the medical needle-knife, and wherein the distal shaft end is insertable within a working channel of an endoscope insertion tube.

14. The medical instrument of claim 13, wherein the second proximal cable portion has a second centerline, wherein the ring is operatively connected to the second proximal cable portion to rotate the second proximal cable portion substantially about its centerline as the ring is rotated about the longitudinal axis of the medical-instrument-handle body relative to any other portion of the medical-instrument-handle body, and wherein the ring is adapted to rotate the first and second proximal cable portions in a same rotational direction.

15. The medical instrument of claim 13, wherein the first proximal cable portion is an RF-energizable cable portion.

16. The medical instrument of claim 12, wherein the second distal cable portion is attached to the first distal cable portion, wherein the attached first and second distal cable portions define a distal-loop medical snare, wherein the medical end effector includes the medical snare, and wherein the distal shaft end is insertable within a working channel of an endoscope insertion tube.

17. The medical instrument of claim 16, wherein the second proximal cable portion has a second centerline, wherein the ring is adapted to rotate the second proximal cable portion about the second centerline, and wherein the ring is adapted to rotate the first and second proximal cable portions in a same rotational direction.

18. The medical instrument of claim 16, wherein the first proximal cable portion is an RF-energizable cable portion.

19. The medical instrument handle of claim 9, wherein the first slide and the second slide are movable together to extend and retract the medical-instrument member, and the first slide and the second slide are movable relative to one another where distally moving only the first slide or only the second slide distally moves only the first articulation cable or only the second articulation cable respectively and proximally moving only the first slide or only the second slide proximally moves only the first articulation cable or only the second articulation cable respectively.

* * * * *